US006462255B1

(12) United States Patent
Turpen

(10) Patent No.: US 6,462,255 B1
(45) Date of Patent: *Oct. 8, 2002

(54) VIRAL AMPLIFICATION OF RECOMBINANT MESSENGER RNA IN TRANSGENIC PLANTS

(75) Inventor: Thomas H. Turpen, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/414,916

(22) Filed: Oct. 8, 1999

Related U.S. Application Data

(63) Continuation of application No. 08/336,724, filed on Nov. 9, 1994, now Pat. No. 5,965,794, which is a continuation of application No. 07/997,733, filed on Dec. 30, 1992, now abandoned.

(51) Int. Cl.$^7$ .................... C12N 15/83; C12N 15/40; C12N 15/12; A01H 5/00
(52) U.S. Cl. .................... 800/278; 800/285; 800/286; 800/288; 800/317.3; 435/69.4; 435/69.5; 435/91.21; 435/235.1; 435/320.1; 435/468; 536/23.72
(58) Field of Search .................... 536/23.72, 23.6; 435/69.4, 69.5, 91.21, 320.1, 468, 235.1; 800/278, 288, 295, 317.3, 285, 286

(56) References Cited

U.S. PATENT DOCUMENTS 5,965,794 A * 10/1999 Turpen .................... 800/288

FOREIGN PATENT DOCUMENTS

| AU | 7 195 191 | 3/1992 |
|---|---|---|
| EP | 0 067 553 | 12/1982 |
| EP | 0 194 809 | 9/1986 |
| EP | 0 278 667 | 8/1988 |
| EP | 0 425 004 | 5/1991 |
| EP | 0 479 180 | 4/1992 |
| EP | 0 573 767 | 12/1993 |
| JP | 63-14693 | 7/1998 |
| WO | 89 08145 | 9/1989 |
| WO | 90 12107 | 10/1990 |
| WO | 91 13994 | 9/1991 |

OTHER PUBLICATIONS

Hartog et al., Chemical Synthesis of a Messager Ribonucleic Acid Fragement, 1982, vol. 21, pp. 1009–1018.*
Mori et al., Infectivity of plasmids containing brome mosaic virus cDNA linked to the cauliflower mosaic virus 35S RNA promoter, 1991, General Virology, vol. 72, pp. 243–246.*
Raffo et al., Construction of Tabacco Mosaic Virus Subgenomic Replicons That Are Replicated and Spread Systemically in Tabacco Plants, 1991, Virology, vol. 184, pp. 277–289.*

Ahlquist et al., "Gene amplification and expression by RNA viruses and potential for furher appication to plant gene transfer", *Physiol. Plant*, vol. 79, 1990, pp. 163–167.
Ahlquist et al., *Viral Vectors*, 1988, pp. 183–189.
Barton et al., *Plant Physiol.*, vol. 85, 1987, pp. 1103–1109.
Butler et al., "Molecular architcture and assembly of tobacco mosaic virus particles", *The Molecular Biology of the Positive Strand RNA Viruses Academic Press*, 1987, pp. 237–257.
Cassidy et al., "Construction and Analysis of a Viral Vector for Rapid Analysis of Gene Expression in Whole Plants", *Phytopathology*, vol. 80, No. 10, 1990, pp. 1037.
Chapman et al., "Potato virus X as a vector for gene expression in plants", *Plant Journal*, vol. 2, No. 4, 1992, pp. 549–557.
Citovsky et al., "How do Plant Virus Nucleic Acids Move Through Intercelluular Conections?", *BioEssays*, vol. 13, N. 8, 1992, pp. 373–379.
Dawson, "Tobamovirus–Plant Interactions", *Virology*, vol. 186, 1992, pp. 359–367.
Dawson, "A Tobacco Mosaic Virus–Hybrid Expresses and Loses an Added Gene", *Virology*, vol. 172, 1989, pp. 285–292.
Dawson, "Regulation of Tobamovirus Gene Expression", *Adv. Virus Res.*, vol. 38,1990, pp. 307–342.
Dawson et al., "Host–Range Determinants of Plant Viruses", *Ann. Rev.*, vol. 43, 1992, pp. 527–555.
Dawson et al., "Modifications of the Tobacco Mosaic Virus coat Protein Gene Affecting Replication, Movement, and Symptomatology", *Phytopathology,* vol. 78, No. 6, 1988, pp. 783–789.
Deom et al., "The 30–Kilodalton Gene Product of Tobacco Mosaci Virus Potentiates Virus Movements", *Science,* vol. 237, 1987, pp. 389–394.

(List continued on next page.)

*Primary Examiner*—David T. Fox
(74) *Attorney, Agent, or Firm*—Albert P. Halluin; Thomas Gallegos; Robin C. Chiang

(57) ABSTRACT

A novel method of over expressing genes in plants is provided. This method is based on the RNA amplification properties of plus strand RNA viruses of plants. A chimeric multicistronic gene is constructed containing a plant promoter, viral replication origins, a viral movement protein gene, and one or more foreign genes under control of viral subgenomic promoters. Plants containing one or more of these recombinant RNA transcripts are inoculated with helper virus. In the presence of helper virus recombinant transcripts are replicated producing high levels of foreign gene RNA. Sequences are provided for the high level expression of the enzyme chloramphenicol acetyltransferase in tobacco plants by replicon RNA amplification with helper viruses and movement protein genes derived from the tobamovirus group.

31 Claims, 8 Drawing Sheets

OTHER PUBLICATIONS

Deom et al., "Plant Virus movement Proteins", *Cell*, vol. 69, 1992, pp. 221–224.

Dolija et al., "Tagging of plant potyvirus replication and movement by insnertion of $_\beta$–glucuonidase into the viral p olyprotein", *Proc. Natl. Acad. Sci.*, vol. 89, 1992, pp. 10208–10212.

Donson et al., "Systemic expression of a bacterial gene by a tobacco mosaic virus–based vector", *Proc. Natl. Acad. Sci.*, vol. 88, 1991, pp. 7204–7208.

Fleischer et al., "Methods in Enzymology," vol. 53, 1973, pp. 737–755.

French et al., "Bacterial Gene Inserted in an Engineered RNA Virus: Efficient Expression in Monocotyledonous Plant Cells", *Science*, vol. 231, 1986, pp. 1294–1297.

Gelvin et al., *Klumer Acedamic Publisher, Dordrecht, The Netherland*, vol. C1, 1988, pp. 1009–1018.

Gelvin et al., *Kluwer Academic Publishers, Dordrecht, The Netherlands*, vol. A5, 1988, pp. 1–9.

Hartog et al., "Chemical Synthesis of a Messager Ribonucleic Acid Fragment", 1982, vol. 21, pp. 1009–1018.

Horsch et al., "Leaf disc tranformation", *Plant Molecular Biology Manual*, vol. A5 1988, pp. 1–9.

Joshi et al., "BSMV genome mediated expression of a foreign genes in dicot and monocot plant cells", *EMBO Jrnl.*, vol. 9, 1990, pp. 2663–2669.

Joshi et al., "Strategies for expression of foreign genes in plants", *FEBS Lett.*, vol. 281, 1991, pp. 1–8.

Jupin et al., "Mapping Sequences Required for Productive Replication of Beet Necrotic Yellow Vein Virus RNA 3", *Virology*, vol. 178, No. 1, 1990, pp. 273–280.

Larkins et al., *J. Cell. Biochem. Suppl. O.*,vol. 9, Part C, 1985, p. 264.

Martelli, "Classification and Nomenclature of Plant Viruses: State of the Art", *Plant Disease*, vol. 76, No. 5, 1992, p. 436.1

Mori et al., Inflectivity of plasmids containing brome mosaic virus cDNA Linked to the cauliflower mosaic virus 35S RNA promoter, *Jrnl. gen. Virology*, vol. 72, No. 2, 1991, pp. 243–246.

Mori et al., *Jrnl. Gen. Virol*, vol. 73, No. 1, 1992, pp. 169–172.

Ogawa et al., "Trans Complementation of Virus–Encoded Replicase components of Tobacco Mosaic Virus" *Virology*, vol. 185, 1991, pp. 580–584.

Ow et al., "Transient and stable Expression of the Firefly Luciferase Gene in Plant Cells and Transgenic Plants", *Science*, vol. 234, 1986, pp. 856–859.

Potrykus, "Gene transfer to Plants: Assessment of Published Approaches and Results", *Annual Rev. Plant Physiol. Plant Mol. Biol.*, vol. 42, 1991, pp. 205–225.

Raffo et al., "Construction of Tobacco Mosaic Virus Subgenomic Replicons that are Replicated and Spread Sysstemically in Tobacco Plants", Virology, vol. 184, 1991, pp. 277–289.

Rowlands et al., *Academic Press*, London, 1987, pp. 237–257.

Saito et al., "Long–Distance movement and Viral Assembley of Tobacco Mosaic Virus Mutants", *Virology*, vol. 176, 1990, pp. 329–336.

Shaw, "Chlorampheniol acetyltransferase from chloramphenicol–resistant bacteria", *Methods in Enzymology*, vol. 53, 1975, pp.737–755.

Takamatsu et al., "Expression of bacterial chloramphenicol acetyltransferase gene in tobacco plants mediated by TMV–RNA", *EMBO Jrnl.*, vol. 6, 1987, pp. 307–311.

Takamatsu et al., "Mutational Analysis of the Pseudoknot Region in the 3'Noncoding Region of Tobacco Mosaic Virus RNA", *Jrnl. Virology*, vol. 64, 1990, pp. 3686–3693.

Takamatsu, "Deletion Analysis of the 5'Untranslated Leader Sequence of Tobacco Mosaic Virus RNA", *Jrnl. Virol.*, vol. 65, 1991, pp. 1619–1622.

Takamatsu et al., "Production of enkephalin in tobacco protoplasts using tobacco mosaic virus RNA vector", FEBS Letters, vol. 269, 1990, pp. 73–76.

Turpen, Ph.D., Dissertation, Univeristy of California, Riverside, 1992, pp. 72–87.

Turpen, Ph.D., Dissertation, Univeristy of California, Riverside, 1992, pp. 85–105.

Turpen, Ph.D., Dissertation, Univeristy of California, Riverside, 1992, pp. 106–132.

Turpen et al., "Amplification, movement and expression of genes in plants by viral–based vectors"*Transgenic plants: fundamentals and applications*, 1992, pp. 195–217.

Van Haute et al., "Intergenic transfer and exchange recombinatin of restriction fragments cloned in pBR322: a novel strategy for the reversed genetics of the Ti plasmids of *Agrobacterium tumefaciens*", *EMBO Jrnl.*, vol. 2, 1983, pp. 411–417.

Velton et al., "Selection–expressioin plasmic vectors for use in genetic transformation of higher plants", *NAR*, vol. 13, No. 19, 1985, pp. 6981–6998.

Walden et al., "Techniques in plant molecular biology–progress and problems", *Eur. Jrnl. Biochem*, vol. 192, No. 3,, 1990, pp. 563–576.

Yamaya et al., "Expression of tobacco mosaic virus RNa in transgenic plants", *Mol. Gen. Genet.*, vol. 211, 1988, pp. 520–525.

Zaitlin et al., "Plant Virus–host Interactions", *Ann. Rev. Plant Physiol.*, vol. 38, 1987, pp. 291–315.

Zambryski et al., "Ti plasmic vector for the introduction of DNA Into plant cells without alteration of their nomrla regeneration capacity", *EMBO Jrnl.*, vol. 2, 1983, pp. 2143–2150.

* cited by examiner

TRANSGENE (cDNA)

TRANSCRIPTION

TRANSCRIPT (RNA)

RNA PROCESSING AND RNA REPLICATION

REPLICON (RNA)

P = PROMOTER

5'RO = 5' REPLICATION ORIGIN

FG = SEQUENCE CODING FOR FOREIGN GENE AS WELL AS OTHER SEQUENCES. DOES NOT CODE FOR COMPLETE SET OF VIRAL REPLICATION PROTEINS REQUIRED FOR REPLICATION.

3' RO = 3' REPLICATION ORIGIN

TT = TRANSCRIPTION TERMINATION SEQUENCE

FIG. 6-1

```
  1 guauuuuuacaacaauuaccaacaacaacaaacaacaaacaacauuacaauuacuauuua  60
 61 caauuacau AUG GCU CUA GUU GUU AAA GGA AAA GUG AAU AUC AAU  105
  1           M   A   L   V   V   K   G   K   V   N   I   N    12

106 GAG UUU AUC GAC CUG ACA AAA AUG GAG AAG AUC UUA CCG UCG AUG  150
 13 E   F   I   D   L   T   K   M   E   K   I   L   P   S   M   27

151 UUU ACC CCU GUA AAG AGU GUU AUG UGU UCC AAA GUU GAU AAA AUA  195
 28 F   T   P   V   K   S   V   M   C   S   K   V   D   K   I   42

196 AUG GUU CAU GAG AAU GAG UCA UUG UCA GAG GUG AAC CUU UUU AAA  240
 43 M   V   H   E   N   E   S   L   S   E   V   N   L   F   K   57

241 GGA GUU AAG CUU AUU GAU AGU GGA UAC GUC UGU UUA GCC GGU UUG  285
 58 G   V   K   L   I   D   S   G   Y   V   C   L   A   G   L   72

286 GUC GUC ACG GGC GAG UGG AAC UUG CCU GAC AAU UGC AGA GGA GGU  330
 73 V   V   T   G   E   W   N   L   P   D   N   C   R   G   G   87

331 GUG AGC GUG UGU CUG GUG GAC AAA AGG AUG GAA AGA GCC GAC GAG  375
 88 V   S   V   C   L   V   D   K   R   M   E   R   A   D   E   102

376 GCC ACU CUC GGA UCU UAC UAC ACA GCA GCU GCA AAG AAA AGA UUU  420
103 A   T   L   G   S   Y   Y   T   A   A   A   K   K   R   F   117

421 CAG UUC AAG GUC GUU CCC AAU UAU GCU AUA ACC ACC CAG GAC GCG  465
118 Q   F   K   V   V   P   N   Y   A   I   T   T   Q   D   A   132

466 AUG AAA AAC GUC UGG CAA GUU UUA GUU AAU AUU AGA AAU GUG AAG  510
133 M   K   N   V   W   Q   V   L   V   N   I   R   N   V   K   147

511 AUG UCA GCG GGU UUC UGU CCG CUU UCU CUG GAG UUU GUG UCG GUG  555
148 M   S   A   G   F   C   P   L   S   L   E   F   V   S   V   162

556 UGU AUU GUU UAU AGA AAU AAU AUA AAA UUA GGU UUG AGA GAG AAG  600
163 C   I   V   Y   R   N   N   I   K   L   G   L   R   E   K   177
                                        Origin of Assembly
601 AUU ACA AAC GUG AGA GAC GGA GGG CCC AUG GAA CUU ACA GAA GAA  645
178 I   T   N   V   R   D   G   G   P   M   E   L   T   E   E   192

646 GUC GUU GAU GAG UUC AUG GAA GAU GUC CCU AUG UCG AUC AGG CUU  690
193 V   V   D   E   F   M   E   D   V   P   M   S   I   R   L   207

691 GCA AAG UUU CGA UCU CGA ACC GGA AAA AAG AGU GAU GUC CGC AAA  735
208 A   K   F   R   S   R   T   G   K   K   S   D   V   R   K   222
```

MOVEMENT PROTEI

FIG. 6-2

```
     736 GGG AAA AAU AGU AGU AAU GAU CGG UCA GUG CCG AAC AAG AAC UAU  780
     233 G   K   N   S   S   N   D   R   S   V   P   N   K   N   Y    237

781 AGA AAU GUU AAG GAU UUU GGA GGA AUG AGU UUU AAA AAG AAU AAU  825
     238 R   N   V   K   D   F   G   G   M   S   F   K   K   N   N    252

826 UUA AUC GAU GAU GAU UCG GAG GCU ACU GUC GCC GAA UCG GAU UCG  870
     253 L   I   D   D   D   S   E   A   T   V   A   E   S   D   S    267

871 UUU UAA auacgcucgacgagauuuucaggagcuaaggaagcuaaa AUG GAG AAA  924
     263 F   *                                           M   E   K    3

925 AAA AUC ACU GGA UAU ACC ACC GUU GAU AUA UCC CAA UCG CAU CGU  969
       4 K   I   T   G   Y   T   T   V   D   I   S   Q   S   H   R     18

970 AAA GAA CAU UUU GAG GCA UUU CAG UCA GUU GCU CAA UGU ACC UAU 1014
      19 K   E   H   F   E   A   F   Q   S   V   A   Q   C   T   Y     33

1015 AAC CAG ACC GUU CAG CUG GAU AUU ACG GCC UUU UUA AAG ACC GUA 1059
      34 N   Q   T   V   Q   L   D   I   T   A   F   L   K   T   V     48

1060 AAG AAA AAU AAG CAC AAG UUU UAU CCG GCC UUU AUU CAC AUU CUU 1104
      49 K   K   N   K   H   K   F   Y   P   A   F   I   H   I   L     63

1105 GCC CGC CUG AUG AAU GCU CAU CCG GAA UUC CGU AUG GCA AUG AAA 1149
      64 A   R   L   M   N   A   H   P   E   F   R   M   A   M   K     78

1195 GUU UUC CAU GAG CAA ACU GAA ACG UUU UCA UCG CUC UGG AGU GAA 1239
      94 V   F   H   E   Q   T   E   T   F   S   S   L   W   S   E    108

1240 UAC CAC GAC GAU UUC CGG CAG UUU CUA CAC AUA UAU UCG CAA GAU 1284
     109 Y   H   D   D   F   R   Q   F   L   H   I   Y   S   Q   D    123

1285 GUG GCG UGU UAC GGU GAA AAC CUG GCC UAU UUC CCU AAA GGG UUU 1329
     124 V   A   C   Y   G   E   N   L   A   Y   F   P   K   G   F    138

1330 AUU GAG AAU AUG UUU UUC GUC UCA GCC AAU CCC UGG GUG AGU UUC 1374
     139 I   E   N   M   F   F   V   S   A   N   P   W   V   S   F    153

1375 ACC AGU UUU GAU UUA AAC GUG GCC AAU AUG GAC AAC UUC UUC GCC 1419
     154 T   S   F   D   L   N   V   A   N   M   D   N   F   F   A    168

1420 CCC GUU UUC ACC AUG GGC AAA UAU UAU ACG CAA GGC GAC AAG GUG 1464
     169 P   V   F   T   M   G   K   Y   Y   T   Q   G   D   K   V    183
```

CAT PROTEIN ↓

FIG. 6-3

```
1465 CUG AUG CCG CUG GCG AUU CAG GUU CAU CAU GCC GUC UGU GAU GGC 1509
 184 L   M   P   L   A   I   Q   V   H   H   A   V   C   D   G   198

1510 UUC CAU GUC GGC AGA AUG CUU AAU GAA UUA CAA CAG UAC UGC GAU 1554
 199 F   H   V   G   R   M   L   N   E   L   Q   Q   Y   C   D   213

1555 GAG UGG CAG GGC GGG GCG UAA uuuuuuuaaggcaguuauuggugcccuuaaac 1607
 214 E   W   Q   G   G   A   *                                   220

1608 gccuggugcuacgccugaauaagugauaauaagcggaugaauggcagaaauucgucgagg 1667
1668 guagucaagaugcauaauaaauaacggauuguguccguaaucacacguggugcguacgau 1727
1728 aacgcauaguguuuuucccuccacuuaaaucgaaggguugugucuuggaucgcgcgdgguc 1787
1788 aaauguauaugguucauauacauccgcaggcacguaauaaagcgaggggguucgaauccccc 1847
1848 ccguuaccccccgguagggggccca                                    1870
```

VIRAL AMPLIFICATION OF RECOMBINANT MESSENGER RNA IN TRANSGENIC PLANTS

CROSS-REFERENCE TO RELATED APPLICATIONS

The present application is a continuation of application Ser. No. 08/336,724 filed Nov. 9, 1994, now U.S. Pat. No. 5,965,794, which is a continuation of application Ser. No. 07/997,733, filed Dec. 30, 1992, now abandoned.

BACKGROUND OF THE INVENTION

The present invention relates to the field of genetically engineering transgenic plants. More specifically, the invention relates to the use of viral RNA to achieve high level expression of foreign genes in plants.

The use of transgenic plants for high level expression of foreign genes has been targeted as an inexpensive means for mass producing desired products. All higher plants are photoautotrophic, requiring only $CO_2$, $H_2O$, $NO_3^{-1}$, $SO_4^{-2}$, $PO_4^{-3}$ and trace amounts of other elements for growth. From these inexpensive starting materials, plants are capable of synthesizing a variety of valuable products. Progress in utilizing transgenic plants as low cost factories will depend on both the characterization of biosynthetic pathways and on the further development of gene expression technologies.

In the past decade, a number of techniques have been developed to transfer genes into plants (Potrykus, I., *Annual Rev. Plant Physiol. Plant Mol. Biol.* 42:205–225 (1991)). For example, chromosomally integrated transgenes have been expressed by a variety of promoters offering developmental control of gene expression. (Walden and Schell, *Eur. J. Biochem.* 192:563–576 (1990)). This technology has been used primarily to improve certain agronomic traits such as disease resistance or food quality. (Joshi and Joshi, *Febs. Lett.* 281:1–8 (1991)). However, the utility of known transgene methodology is limited by 1) the difficulty of obtaining high level expression of individual transgenes 2) the lack of means necessary for coordinating control of several transgenes in an individual plant 3) the lack of means to enable precise temporal control of gene expression and 4) the lack of adequate means to enable shutting off introduced genes in the uninduced state (Walden and Schell, *Eur. J. Biochem* 192:563–576 (1990)).

The most highly expressed genes in plants are encoded in plant RNA viral genomes. Many RNA viruses have gene expression levels or host ranges that make them useful for development as commercial vectors. (Ahlquist, P., and Pacha, R. F., *Physiol. Plant.* 79:163–167 (1990), Joshi, R. L., and Joshi, V., *FEBS Lett.* 281:1–8 (1991), Turpen, T. H., and Dawson, W. O., Amplification, movement and expression of genes in plants by viral-based vectors, Transgenic plants: fundamentals and applications (A. Hiatt, ed.), Marcel Dekker, Inc., New York, pp. 195–217. (1992)). For example, tobacco (*Nicotiana tabacum*) accumulates approximately 10 mg of tobacco mosaic tombamovirus (TMV) per gram of fresh-weight tissue 7–14 days after inoculation. TMV coat protein synthesis can represent 70% of the total cellular protein synthesis and can constitute 10% of the total leaf dry weight. A single specific RNA transcript can accumulate to 10% of the total leaf mRNA. This transcript level is over two orders of magnitude higher than the transcription level observed for chromosomally integrated genes using conventional plant genetic engineering technology. This level of foreign gene expression has not yet been obtained using the prior art viral vectors in plants.

Most plant viruses contain genomes of plus sense RNA (messenger RNA polarity) (Zaitlin and Hull, *Ann. Rev. Plant Physiol.* 38:291–315 (1987)). Plus sense plant viruses are a very versatile class of viruses to develop as gene expression vectors since there are a large number of strains from some 22 plus sense viral groups which are compatible with a wide number of host plant species. (Martelli, G. P., *Plant Disease* 76:436 (1992)). In addition, an evolutionarily related RNA-dependent RNA polymerase is encoded by each of these strains. This enzyme is responsible for genome replication and mRNA synthesis resulting in some of the highest levels of gene expression known in plants.

In order to develop a plant virus as a gene vector, one must be able to manipulate molecular clones of viral genomes and retain the ability to generate infectious recombinants. The techniques required to genetically engineer RNA viruses have progressed rapidly. If the virus is an RNA virus, the virus is generally cloned as a cDNA and inserted into a plasmid. The plasmid is used to make all of the constructions. The genome of many plus sense RNA viruses can be manipulated as plasmid DNA copies and then transcribed in vitro to produce infectious RNA molecules (reviewed in Turpen and Dawson, Transgenic Plants, Fundamentals and Applications, Marcel Dekker, New York, pp. 195–217 (1992)).

The interaction of plants with viruses presents unique opportunities for the production of complex molecules as typified by the TMV/tobacco system (Dawson, W. O., *Virology* 186:359–367 (1992)). Extremely high levels of viral nucleic acids and/or proteins accumulate in infected cells in a brief period of time. The virus catalyzes rapid cell-to-cell movement of its genome throughout the plant, with no significant tissue tropism. The infection is maintained throughout the life of the plant. The plants are not significantly adversely affected by the viral infection since the virus causes little or no general cytotoxicity or specific suppression of host gene expression.

The tobacco mosaic tobamovirus is of particular interest to the instant invention in light of its ability to express genes at high levels in plants. TMV is a member of the tobamovirus group. TMV virions are 300 nm×18 nm tubes with a 4 nm-diameter hollow canal, and consist of 2140 units of a single structural protein helically wound around a single RNA molecule. The genome is a 6395 base plus-sense RNA. The 5'-end is capped and the 3'-end contains a series of pseudoknots and a tRNA-like structure that will specifically accept histidine. The genomic RNA functions as mRNA for the production of proteins involved in viral replication: a 126-kDa protein that initiates 68 nucleotides from the 5'-terminus and a 183-kDa protein synthesized by readthrough of an amber termination codon approximately 10% of the time (FIG. 1). Only the 183-kDa and 126-kDa viral proteins are required for TMV replication in trans. (Ogawa, T., Watanabe, Y., Meshi, T., and Okada, Y., *Virology* 185:580–584 (1991)). Additional proteins are translated from subgenomic size mRNA produced during replication (reviewed in Dawson, W. O., *Adv. Virus Res.* 38:307–342 (1990)). The 30-kDa protein is required for cell-to-cell movement; the 17.5-kDa capsid protein is the single viral structural protein. The function of the predicted 54-kDa protein is unknown.

The minimal sequences required in cis for TMV replication are located at the extreme 5' and 3' noncoding regions (replication origins), as determined by analysis of deletion mutants in plant protoplasts (Takamatsu, N., et al., *J. Virol.* 64:3686–3693 (1990), Takamatsu, N., et al., *J. Virol.* 65:1619–1622 (1991)). In whole plants, helper-dependent RNA replicons, constructed by deletion of most of the 126/183-kDa replication protein sequence and most of the 30-kDa movement protein sequence, are replicated and spread systemically in the presence of wild type TMV (Raffo A. J., and Dawson W. O., *Virology* 184:277–289 (1991)).

Turpen, et al. discloses a simple and reliable gene transfer method wherein cDNA of TMV is engineered into A. tumefaciens for expression in plant cells (Turpen, T. H., Ph.D. Dissertation, University of California, Riverside, pp. 88–105 (1992)). This method provides an alternative to the use of synthetic infectious transcripts to inoculate plants based on host transcription of viral cDNA in vivo. Turpen showed successful transfection of tobacco (*N. tabacum* cv. Xanthi and Xanthi/nc) with wild type and defective viral genomes using this methodology.

Transfection also occurs spontaneously in transgenic lines containing defective or wild type cDNA of TMV integrated chromosomally (Turpen, T. H., Ph.D. Dissertation, University of California, Riverside, pp. 106–132 (1992), Yamaya, J., et al., *Mol. Gen. Genet.* 211:520–525 (1988)). Thus, once chromosomally integrated, viral replication can be derived from the process of host cell transcription.

Plant virus infections are initiated by mechanical damage to the plant cell wall. Following replication in the initially wounded cells, progeny viruses spread over short distances (cell-to-cell movement) before entering vascular tissue for long distance movement. Studies with chimeric tobamoviruses indicate that the coat protein is required for efficient long distance movement. However, a virus where the coat protein has been deleted or inactivated moves over short distances as does wild type virus (Dawson W. O. and Hilf, M. E., *Ann. Rev. Plant Physiol. Plant Mol. Biol.* 43:527–555 (1992)).

In the case of TMV, functional 30-kDa movement protein is absolutely required for cell-to-cell movement in whole plants, but can be deleted or inactivated without affecting replication in protoplasts or inoculated leaves (reviewed in Citovsky, V., Zambryski, P., *BioEssays* 13:373–379 (1991) and Deom, C. M., Lapidot, M., and Beachy, R. N., *Cell* 69:221–224 (1992)).

A sequence located within the 30 kDa movement protein gene of the U1 strain of TMV serves as the origin of assembly. It is at this origin of assembly that the TMV RNA and the viral capsid protein spontaneously aggregate to initiate the assembly of virions (Butler, P. J. G., Mayo, M. A., Molecular architecture and assembly of tobacco mosaic virus particles, The molecular biology of the positive strand RNA viruses. (D. J. Rowlands, M. A. Mayo, and B. W. J. Mahy, eds.), Academic Press, London. pp. 237–257 (1987)). A functional origin of assembly is also required for efficient long distance movement (Saito, T., Yamanaka, K., and Okada, Y., *Virology* 176:329–336 (1990)). There does not appear to be any additional requirements for packaging. A variety of heterologous sequences can be encapsidated yielding rod-shaped virions whose lengths are proportional to the size of the RNA molecule containing the origin of assembly (Dawson, W. O. et al., *Virology* 172:285–292 (1989)).

Construction of plant RNA viruses for the introduction and expression of foreign genes in plants is demonstrated by French, R., et al., *Science* 231:1294–1297 (1986); Takamatsu, N., et al., *EMBO J* 6:307–311 (1987); Ahlquist, P., et al., *Viral Vectors,* Cold Spring Harbor Laboratory, New York, 183–189 (1988); Dawson, W. O., et al., *Phytopathology* 78:783–789 (1988); Dawson, W. O., et al., *Virology* 172:285–292 (1989); Cassidy, B., and Nelson, R., *Phytopathology* 80:1037 (1990); Joshi, R. L., et al., *EMBO J.* 9:2663–2669 (1990); Jupin, I., et al., *Virology* 178:273–280 (1990); Takamatsu, N., et al., *FEBS Letters* 269:73–76 (1990); Japaneses Published Application No. 63–14693 (1988); European Patent Application No. 067,553; and European Patent Application No. 194,809, European Patent Application No. 278,667. Most of the viral vectors constructed in these references were not shown to be capable of systemic movement in whole plants. Rather, gene expression has only been confirmed in inoculated leaves. In other cases, systemic movement and expression of the foreign gene by the viral vector was accompanied by rapid loss of the foreign gene sequence (Dawson, W. O., et al., *Virology* 172:285 (1989)).

With further improvements, successful vectors have been developed based on tobamoviruses for rapid gene transfer to plants. (Donson et al., *Proc. Natl. Acad. Sci.* 88:7204–7208 (1991)). For example, the α-trichosanthin gene was added to the genome of a tobamovirus vector under the transcriptional control of a subgenomic promoter obtained from a strain distantly related to wild type TMV (Turpen, T. H., Ph.D. Dissertation, University of California, Riverside, pp. 72–87 (1992)). This vector is an autonomous virus, containing all known viral functions. Two weeks post-inoculation, transfected *Nicotiana benthamiana* plants accumulated α-trichosanthin to levels of at least 2% total soluble protein. Purified recombinant α-trichosanthin produced by this method was correctly processed and had the same specific activity as the enzyme derived from the native source. Therefore, messenger RNA produced by viral RNA amplification in whole plants is fully functional. However, after prolonged replication of certain sequences using this vector, some genetic instability was observed primarily due to recombinational deletions and point mutations (Kearney, C. M., et al., *Virology* (in press)).

Recently, very similar results were obtained using gene vectors derived from additional plus sense RNA viruses infecting plants; a potyvirus, tobacco etch virus ((Dolja, V., et al., *PNAS* 89:10208–10212 (1992) and a potexvirus, potato virus X (Chapman, S., et al., Plant Journal 2:549–557 (1992)).

Therefore, the major functional disadvantages of existing prior art viral vectors are their genetic instability regarding the fidelity of maintenance of some non-viral foreign genes in systemically infected whole plants, after prolonged replication and passaging. For many products, it will be desirable to increase the genetic fidelity by lowering the proportion of deletion and other variants in amplified populations.

An additional concern regarding the use of viral vectors for the expression of foreign genes in transgenic plants is biological containment of the viral vectors encoding for foreign genes.

SUMMARY OF THE INVENTION

The instant invention provides a replicon derived from a chromosomally integrated transgene capable of expressing at least one foreign gene in plant cells. The replicon possesses replication origins with substantial sequence homology to a plus sense, RNA virus capable of infecting plants. The replicon is dependent for replication on a helper virus possessing trans-acting replication proteins where the replication proteins have substantial sequence homology to the replication proteins of a plus sense, RNA virus capable of infecting plants.

In still another aspect of the invention, the replicon additionally codes for a viral sequence upon which a helper virus is dependent in trans. In a yet further aspect of the present invention, the additional viral sequence coded for by the replicon is a viral movement protein.

In another aspect of the present invention, the replicon is also capable of moving the replicon-encoded genes away from the site of infection and is also capable of systemic expression.

The present invention also provides heterologous proteins and RNA sequences expressed in plants using one of the replicons of the instant invention.

The present invention also provides primary or secondary metabolites that accumulate in the tissues of a transfected plant as a result of the expression of a foreign gene product coded for by one of the replicons of the instant invention.

The present invention also provides transgenic plants that contain a chromosomally integrated transgene that codes for one of the replicons of the instant invention.

The present invention also provides a method for expressing a foreign gene in plants by integrating a transgene coding for one of the replicons of the instant invention into the host DNA of a plant cell and infecting the plant cell with a helper virus.

The present invention also provides a method for expressing a foreign gene in plants by integrating a transgene coding for one of the replicons of the instant invention into the host DNA of a plant cell and infecting the plant cell with a helper virus wherein the helper virus is dependent in trans on the replicon.

The present invention also provides a method for expressing a foreign gene in plants by integrating a transgene coding for one of the replicons of the instant invention into the host DNA of a plant cell and infecting the plant cell with a helper virus wherein the helper virus is dependent in trans on the replicon for expression of a movement protein.

In further embodiments of the present invention, expression of the foreign gene by the replicon is regulatable. In another, preferred embodiment of the replicon, the foreign gene sequence on the replicon is placed 5' to the 3' replication origin. In further preferred embodiments, the movement protein is derived from a tobamovirus and more specifically, a TMV strain virus.

BRIEF DESCRIPTION OF THE DRAWINGS

FIG. 6 is the sequence of the RNA replicon described in Example 1.

DEFINITIONS

Foreign gene: A "foreign gene" refers to any sequence that is not native to the virus.
In cis: "In cis" indicates that two sequences are positioned on the same strand of RNA or DNA.
In trans: "In trans" indicates that two sequences are positioned on different strands of RNA or DNA.
Movement protein: A "movement protein" is a noncapsid protein required for cell to cell movement of replicons or viruses in plants.
Origin of Assembly: An "origin of assembly" is a sequence where self-assembly of the viral RNA and the viral capsid protein initiates to form virions.
Replication origin: A "replication origin" refers to the minimal terminal sequences in linear viruses that are necessary for viral replication.
Replicon: A "replicon" is an arrangement of RNA sequences generated by transcription of a transgene that is integrated into the host DNA that is capable of replication in the presence of a helper virus. A replicon may require sequences in addition to the replication origins for efficient replication and stability.
Transcription termination region: The "transcription termination region" is a sequence that controls formation of the 3' end of the transcript. Self-cleaving ribozymes and polyadenylation sequences are examples of transcription termination sequences.
Transgene: A "transgene" refers to the DNA sequence coding for the replicon that is inserted into the host DNA.
Virion: A "virion" is a particle composed of viral RNA and viral capsid protein.

DETAILED DESCRIPTION OF THE INVENTION

The instant invention provides high level expression of foreign genes in plants by viral replicons wherein the replicons possess improved genetic stability. The replicons of the instant invention are produced in host plant cells by transcription of integrated transgenes. The replicons of the instant invention are derived, in part, from single stranded plus sense plant RNA viruses.

Figure 2A:
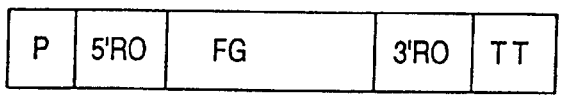
FIG. 2A–2C depict the essential features of the instantly claimed viral replicons.
Figure 2B:
Figure 2C:
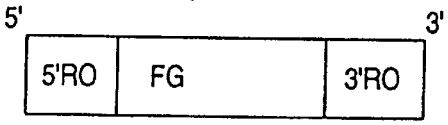

The replicons of the instant invention code for at least one foreign gene and possess sequences required in cis for replication ("replication origins"). FIG. 2(c). The replicons are produced by host cell transcription of a chromosomally integrated transgene to form an RNA transcript. The transgene is a DNA sequence that codes for the replicon and also contains a promoter and a transcription termination region. FIG. 2(a). The replicon is generated from an RNA transcript of the transgene by RNA processing and replication in the presence of a helper virus. FIG. 2(b).

The replicons of the instant invention lack functional replication protein sequences. Because the replicons of the instant invention lack replication protein sequences, they must rely on genetic complementation with helper viruses for replication. The replicon's dependency on the helper virus for replication enables regulatable amplification of these replicons through the introduction of the helper virus.

Genetic complementation of the replicon with a helper virus provides many advantages over autonomous viral vectors for amplifying gene expression. Each infected cell of a transgenic plant contains a correct master copy of the gene to be amplified. This reduces the effects of genetic drift in replicating RNA populations that can result in sequence instabilities and point mutations after prolonged replication of an RNA vector (Kearney, C. M., et al., *Virology* (in press)).

Figure 3:
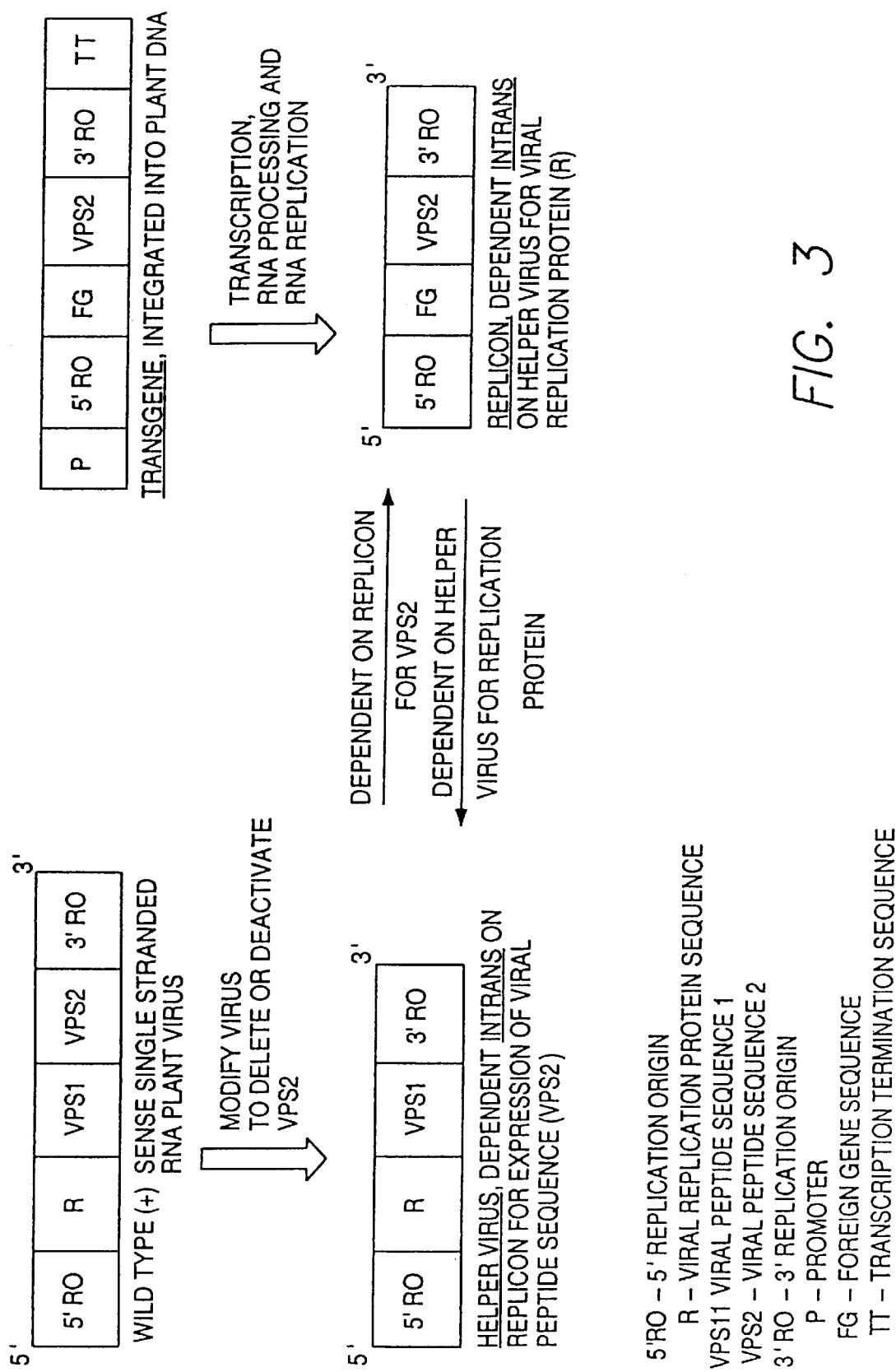
FIG. 3 depicts an embodiment where the replicon and helper virus are mutually dependent.

In a further embodiment of the instant invention, the replicon codes for at least one sequence upon which the helper virus is dependent. Thus, in this further embodiment, the replicon and the helper virus are mutually dependent. [See FIG. 3]. Helper virus dependence on the replicon insures amplified expression of the replicon sequences by the helper virus in whole plants.

In a further embodiment, the replicon codes for a functional movement protein such as the 30 kDa TMV movement protein. The helper virus used in this embodiment does not possess a functional movement protein. Thus, the helper virus is dependent on the replicon for movement functionality. Movement proteins are necessary for cell to cell movement in plants. By placing a functional movement protein sequence on the replicon and either deactivating or deleting the same sequence on the helper virus or by using a host species with helper virus encoded movement protein incompatibility, the helper virus's dependency on the replicon enables systemic infection of the whole plant with the viral replicon plus helper virus.

This embodiment of the instant invention has the further advantage that the only virus released into the environment will be a debilitated helper virus. Thus, the helper virus will not be able to spread in plants that do not already contain a functional copy of the viral movement protein. This embodiment provides an option for more stringent levels of biological containment which may be desirable in some cases for large scale commercial production.

Figure 4:
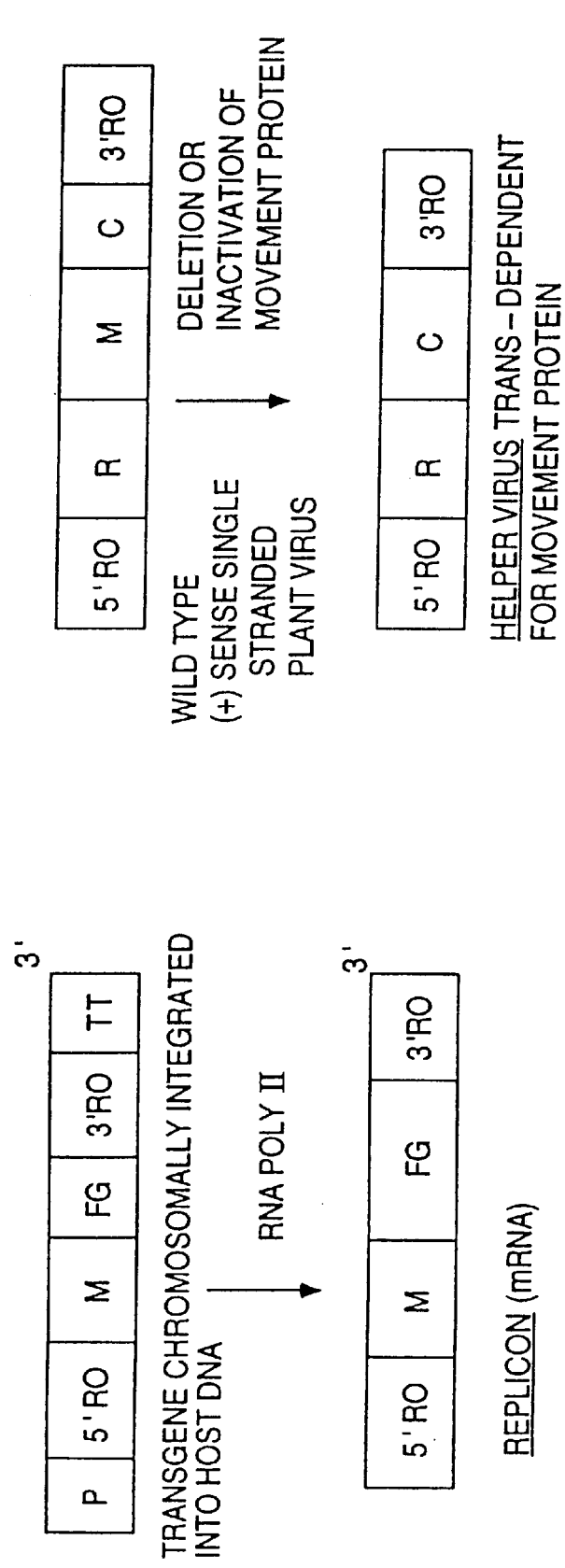
FIG. 4 depicts a preferred replicon gene arrangement where the foreign gene is situated at the 3' end of the genome 5' to the 3' replication origin.

In a preferred embodiment, the replicon is formulated such that the sequences encoding the replication origins and the movement functions are linked to the foreign gene sequences. The chromosomally integrated transgene that codes for the replicon is transcribed by host RNA polymerase II producing recombinant mRNAs. In the presence of a helper virus, these transcripts are replicated as additional replicon components in a mixed population. During viral replication, subgenomic messenger RNA may be produced from replicon RNA resulting in amplified expression of foreign genes. The most preferred replicon gene arrangement places the foreign gene at the extreme 3' end of the genome where the viral structural protein is normally encoded. See FIG. 4. This position for the foreign gene at the extreme 3' end of the genome, as depicted in FIG. 4, is critical for high level expression (Culver, J. N., et al., *Virology* (in press)). However, the protein coding sequences or other gene sequences located between the replication origins may be functional in any order.

Additional preferred embodiments of the replicon sequence include the use of regulatable promoters to control expression of the foreign gene and/or movement protein. One promoter for expression of a fusion protein containing the foreign protein or a series of subgenomic promoters may be employed. Self-cleaving ribozymes or a polyadenylation region may also be employed as the transcription termination regions.

The replicons are generated in vivo in plants through transcription of transgenes that are integrated into the host plant cell chromosome and through replication in the presence of a helper virus. The transgenes can be introduced into the host plant cell chromosome by known transformation methods using a variety of promoters. After the replicon has been introduced into the host, the resulting transgenic plants are grown to an optimized stage at which point a helper virus strain is added. The replicons are then amplified by the introduced helper virus and the foreign gene is expressed.

The foreign gene product coded for and expressed by the replicon can be a very wide variety of RNA or proteins products and include, for example, antisense and ribozyme RNA, regulatory enzymes, and structural, regulatory and therapeutic proteins that may be expressed in their native form or as gene fusions. Typical therapeutic proteins include members of the interleukin family of proteins and colony stimulating factors such as CSF-G, CSF-GM and CSF-M. It is understood, however, that any therapeutic protein can be coded for and expressed in the instant invention.

If expression of the foreign gene results in the accumulation of a protein or other material in the plant tissues, that resulting product may be harvested once the desired concentration of that product is achieved. Significant quantities of recombinant proteins, nucleic acids or other metabolites can be inexpensively produced using this procedure. The low level of expression and wide variation that is observed in transgenic organisms chromosomally transformed with the same construct (a phenomenon attributed to "position effects"), is avoided by this method. RNA-based amplification is not critically dependent on initial transcript amounts. There is also no theoretical limit to the number of genes that can be amplified at the RNA level. The target gene remains "off" before amplification because subgenomic mRNA is only produced during viral replication. Therefore this approach might be particularly appropriate for controlling complex biochemical pathways or producing products that are toxic to the plant. It would be feasible for example, to overexpress critical enzymes in a pathway and simultaneously down-regulate other genes by amplifying antisense RNA only after inoculation with a helper virus. These types of manipulations are not possible using existing or proposed technologies for chromosomal transformation of plants or plant cell cultures or by using prior art viral vectors.

DESCRIPTION OF THE PREFERRED EMBODIMENTS

The following examples further illustrate the present invention.

EXAMPLE 1

Construction of a Transgene for Expression of Recombinant Messenger RNA

Figure 1:
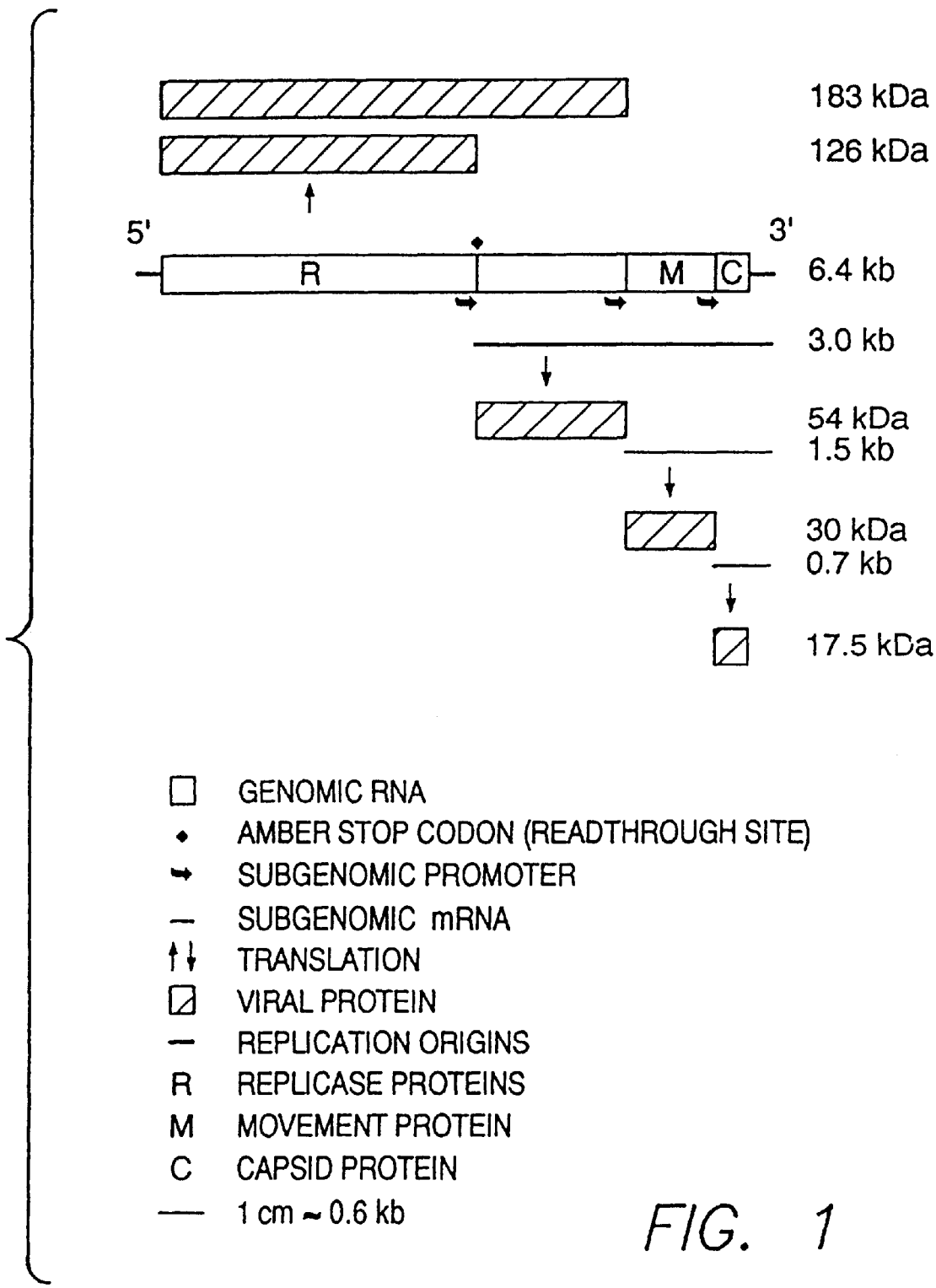
FIG. 1 depicts the genome of wild type TMV.

Construction of a transgene derived from TMV is set forth herein. The wild type TMV genome is set forth in FIG. 1. The construction of DNA plasmids containing the 5' replication origin fused to the CaMV 35S promoter are described in (Ow, D. W., et al., *Science* 234:856–859 (1986)) and the 3' replication origin fused to a ribozyme termination region are described by Turpen, T. H., Ph.D. Disertation, University of California, Riverside, pp. 88–105 (1992).

The substitution of the coat protein gene for the coding sequence of CAT is described in Dawson, et al., *Phytopathol.* 78:783–789 (1988). These previously disclosed plasmids, pBGC43, pBGC44, pBGC75 (Turpen, T. H., Ph.D. Disertation, University of California, Riverside, pp. 88–105 (1992)) and pTMVS3CAT28 (Dawson, et al., *Phytopathol.* 78:783–789 (1988)) are used as precursors for the construction of the desired transgene for synthesis of replicon RNA (FIG. 5).

Figure 5:
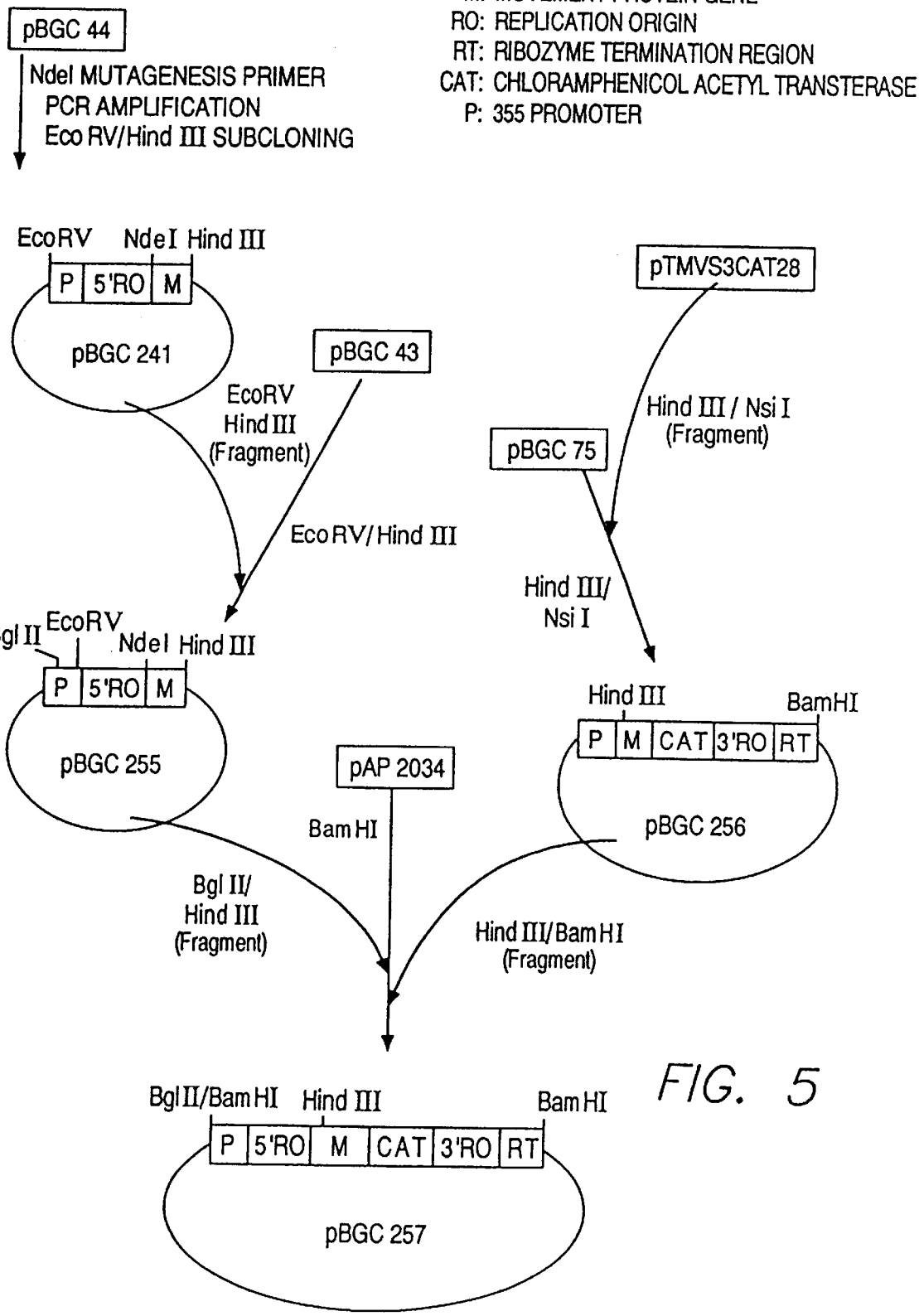
FIG. 5 depicts the construction of a transgene for the synthesis of a replicon encoding Chloramphenicol Acetyltransferase (CAT) in an Agrobacterium transformation vector.

In this construction, it is desired to place the 30-kDA movement protein gene at precisely the same position as the replicase gene (relative to 5' replication origin in the wild type TMV genome, See FIG. 5). To accomplish this, a NdeI site is introduced at the start codon of each gene by PCR-based mutagenesis using synthetic primers and unique adjacent cloning sites. A 270 bp mutagenesis product containing the internal NdeI site from the PCR primer is subcloned using the EcoRV site in the cauliflower mosaic virus 35S promoter and the HindIII site in the 30-kDa protein gene. The ligation product is then sequence verified.

The 3' segment of the replicon, containing the CAT gene will be placed adjacent to the 3' -ribozyme as a HindIII-NsiI fragment from the transient TMV vector pTMVS3CAT28 (FIG. 5). In the final cloning step, the 5' portion of the transgene and the 3' portion will be subcloned into the unique BamHI site of the plant transformation vector pAP2034 (Velton and Schell, *NAR* 13:6981–6998 (1985)) as a BglII-BamHI fragment described previously (Turpen, T. H., Ph.D. Disertation, University of California, Riverside, pp. 88–132 (1992)). The sequence of the replicon RNA, produced by host transcription, RNA processing, and replication in the presence of a helper virus, is given in FIG. 6. Thus, the foreign gene (CAT) is placed on a RNA viral replicon, under control of the coat protein subgenomic promoter for messenger RNA synthesis (located at the 3' end of the movement protein gene).

EXAMPLE 2

Transformation of Plants

In one embodiment of this invention, *Agrobacterium tumefaciens* is used for insertion of this sequence into the plant chromosome as described previously (Turpen, T. H., Ph.D. Dissertation, University of California, Riverside, pp. 106–132 (1992)). The transformation vector pAP2034 is a cointegrating type Agrobacterium vector. pAP2034 containing the transcription unit for the production of replicon RNA is mobilized into *A. tumefaciens* by conjugation using the helper strain GJ23 (Van Haute, E., Joos, et al., *EMBO J.* 2:411–417 (1983)). Transconjugants are selected and the structure of the cointegrate between donor plasmid and the disarmed Ti plasmid pGV3850 (Zambryski, P., et al., *EMBO J.* 2:2143–2150 (1983)) is confirmed by Southern blot hybridization. A correct homologous recombination event places the transgene construct between the TDNA borders.

Axenic leaf segments of *N. tabacum* cv. Xanthi are treated (Horsch, R. B., et al., Leaf disc transformation, *Plant molecular biology manual.* (S. B. Gelvin, R. A. Schilperoort, and D. P. S. Verma, eds.), Kluwer Academic Publishers, Dordrecht, The Netherlands, pp. A5:1–9 (1988)) in the following sequence: day 1; leaf segments are dipped in *A. tumefaciens* liquid culture and placed on regeneration media (RM), day 3; explants are transferred to RM supplemented with cefotaxime (500 μg/ml), day 5; explants are transferred to RM/cefotaxime (500 μg/ml)+ kanamycin (100 μg/ml), day 30–40; shoots excised and placed onto rooting media containing cefotaxime (500 μg/ml) and kanamycin (100 μg/ml). Cultures are maintained under continuous fluorescent light (Sylvania GTE, Gro-Lux WS) at 20° C.

Hardened plants are grown in commercial potting soil (Cascade Forest Products Inc., Arcata, Calif.) at a temperature of 21–29° C., with a controlled release fertilizer (Osmocote, 14-14-14) using natural light (Vacaville, Calif.) supplemented with fluorescent light on a 16 hr day length in an indoor greenhouse. The antibiotic resistance trait carried in transgenic lines is scored by germinating seedlings in sterile agar in the presence of 100 μg/ml kanamycin (Dunsmuir, P., et al., Stability of introduced genes and stability of expression, *Plant molecular biology manual.* (S. B. Gelvin, R. A. Schilperoort, and D. P. S. Verma, eds.), Kluwer Academic Publishers, Dordrecht, The Netherlands, pp. C1:1–17 (1988)).

EXAMPLE 3

Production of Replicon RNA in the Presence of Helper Virus

The sequence of the replicon RNA, produced by host transcription, RNA processing, and replication in the presence of a helper virus, is given in FIG. 6. Tobamoviruses with mutations or naturally occurring variation in the 30-kDa protein gene are deficient in cell-to-cell movement on specific host species. Transgenic plants or alternate hosts can complement this defect. It will be appreciated to those skilled in the art that there are numerous methods of producing helper tobamoviruses by genetic engineering or by mutagenesis in addition to those helper variants or host species combinations occurring naturally. Likewise, methods for producing transgenic plants which express 30 kDa protein and which complement defective 30 kDa containing viruses have been published. For example, movement deficient helper viruses can be synthesized by transcription of TMV with known mutations for the production of RNA inoculum. Transgenic plants expressing the 30-kDa protein complement this defect (Deom, C. M., et al., *Science* 237:389–394 (1987)). Therefore, large quantities of a helper virus can be propagated. In one embodiment of this invention, a 30-kDa protein frameshift mutant, having a single base pair deletion at position 4931 thereby creating a EcoRV site in the cDNA, is used as helper virus. Transgenic tobacco (~100 plants) are regenerated containing this replicon transgene construction and assayed for CAT activity in the presence and absence of helper viruses using procedures described (Shaw, W. V., Chloramphenicol acetyltransferase from chloramphenicol-resistant bacteria, *Methods in Enzymology,* Vol. 53, (S. Fleischer and L. Packer, eds.), pp. 737–755 (1975)). 200 mg of leaf tissue is macerated in assay buffer followed by the addition of 0.5 mM acetyl CoA and 0.1 uCi [$^{14}$C] chloramphenicol, incubation for 45 min at 37° C., extraction, resolution by thin-layer chromatography, and autoradiography.

While the invention of this patent application is disclosed by reference to the details of preferred embodiments of the invention, it is to be understood that this disclosure is intended in an illustrative rather than limiting sense, as it is contemplated that modifications will readily occur to those skilled in the art, within the spirit of the invention and the scope of the appended claims. It is further understood that the instant invention applies to all viruses infecting plants and plants generally and is not limited to those plasmids, viruses or plants described herein.

What is claimed is:

1. A replicon obtained from a chromosomally integrated transgene, wherein said replicon encodes at least one foreign gene capable of expression in a plant or a plant cell, wherein said replicon possesses a replication origin of a plus sense, RNA virus capable of infecting a plant or a plant cell, wherein said replicon is transcribed from a promoter, wherein the replicon does not express a replicase of said plus sense, RNA virus and is dependent for replication on a helper virus, wherein said helper virus is a plus sense, RNA virus capable of infecting a plant or a plant cell, wherein said helper virus encodes said replicase.

2. A replicon of claim 1 wherein expression of the foreign gene is capable of being regulated.

3. A replicon of claim 1 wherein the foreign gene of said replicon is located 5' to the 3' replication origin.

4. A replicon of claim 1 wherein said replicon codes for a viral protein upon which said helper virus is dependent in trans.

5. A replicon of claim 4 wherein said replicon codes for a viral movement protein.

6. A replicon of claim 5 wherein said viral movement protein is located 3' to the 5' replication origin.

7. A replicon of claim 5 wherein said viral movement protein is capable of moving the replicon-encoded genes away from the site of infection and wherein said viral movement protein is capable of causing systemic expression of said replicon.

8. A replicon of claim 6 wherein the foreign gene of said replicon is located 5' to the 3' replication origin.

9. A replicon of claim 7 wherein expression of said viral movement protein is regulatable.

10. A replicon of claim 7 wherein said movement protein is obtained from a tobamovirus.

11. A replicon of claim 7 wherein said movement protein is obtained from a TMV strain virus.

12. A transgenic plant wherein a transgene coding for the replicon of claim 1 is chromosomally integrated into the host DNA.

13. A method of expressing a foreign gene in plants comprising:

a) integrating a transgene coding for the replicon of claim 1 into the host DNA of a plant cell; and b) infecting the plant cell with a helper virus.

14. The method of claim 13 wherein the helper virus is dependent in trans on the replicon.

15. The method of claim 13 wherein the helper virus is dependent in trans on the replicon for expression of a movement protein.

16. The method of claim 13 wherein expression of the foreign gene is regulatable.

17. The method of claim 15 wherein expression of the movement protein is regulatable.

18. The method of claim 13 wherein said movement protein is obtained from a tobamovirus.

19. The method of claim 13 wherein said movement protein is obtained from a TMV strain virus.

20. A replicon of claim 7 wherein said movement away from the site of infection is regulatable.

21. A replicon comprising a replication origin of a plus-sense RNA plant virus, wherein said replicon does not express a trans-acting replicase necessary for replication of said replicon in a plant cell, wherein said replicon encodes a gene product not native to said plus-sense RNA plant virus, wherein said replicon is transcribed from a promoter, wherein said replicon is capable of replication in a plant cell when said transacting replicase is present in trans to said replicon.

22. A plant comprising a replicon according to claim 21.

23. The plant according to claim 22, wherein said plant comprises a transgene encoding said replicon, wherein said transgene is integrated into the DNA of said plant.

24. The plant according to claim 23, further comprising a helper virus which is a plus-sense RNA plant virus.

25. The plant according to claim 24, wherein said helper virus encodes said trans-acting replicase.

26. The plant according to claim 24, wherein said helper virus does not express a viral movement protein.

27. The plant according to claim 26, wherein said replicon encodes said viral movement protein.

28. The replicon according to claim 21, wherein said heterologous gene product is an antisense RNA, ribozyme RNA, regulatory enzyme, structural protein, regulatory protein, or therapeutic protein.

29. The replicon according to claim 21, wherein said plus-sense RNA plant virus is a tobamovirus.

30. A transgene encoding the replicon according to claim 21.

31. A plant comprising the transgene according to claim 30.

* * * * *